US011013848B2

(12) United States Patent
Häcker et al.

(10) Patent No.: US 11,013,848 B2
(45) Date of Patent: May 25, 2021

(54) METHOD FOR REMOVING FLUID FROM A BLOOD FILTER AFTER COMPLETING A BLOOD TREATMENT SESSION BY MEANS OF FLOW INCREASE AND TREATMENT DEVICE FOR CARRYING OUT SAID METHOD

(71) Applicant: Fresenius Medical Care Deutschland GmbH, Bad Homburg (DE)

(72) Inventors: Jürgen Häcker, Neu-Anspach (DE); Sören Gronau, Rüsselsheim (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 16/590,684

(22) Filed: Oct. 2, 2019

(65) Prior Publication Data

US 2020/0030519 A1 Jan. 30, 2020

Related U.S. Application Data

(62) Division of application No. 15/322,840, filed as application No. PCT/EP2015/064833 on Jun. 30, 2015, now Pat. No. 10,532,144.

(30) Foreign Application Priority Data

Jun. 30, 2014 (DE) .......................... 102014109136.1

(51) Int. Cl.
*A61M 1/36* (2006.01)
*A61M 1/34* (2006.01)

(52) U.S. Cl.
CPC ........ *A61M 1/3646* (2014.02); *A61M 1/3434* (2014.02); *A61M 1/3437* (2014.02); *A61M 1/3465* (2014.02); *A61M 1/3649* (2014.02); *A61M 1/3431* (2014.02); *A61M 2205/123* (2013.01); *A61M 2205/52* (2013.01)

(58) Field of Classification Search
CPC ........................ A61M 1/3646; A61M 2205/52
See application file for complete search history.

(56) References Cited

U.S. PATENT DOCUMENTS

| 2011/0284467 A1 | 11/2011 | Okazaki |
| 2013/0025697 A1 | 1/2013 | Blasek et al. |
| 2013/0079698 A1 | 3/2013 | Bocklet |

FOREIGN PATENT DOCUMENTS

| CN | 1604798 | 4/2005 |
| CN | 102307650 | 1/2012 |
| CN | 102753208 | 10/2012 |

(Continued)

OTHER PUBLICATIONS

English Translation of International Preliminary Report on Patentability in Application No. PCT/EP2015/064833, dated Jan. 3, 2017, 9 pages.

(Continued)

*Primary Examiner* — Bradley R Spies
(74) *Attorney, Agent, or Firm* — Fish & Richardson P.C.

(57) ABSTRACT

The present invention relates to a method for removing a first fluid from a blood filter for the blood treatment of a patient and/or for removing blood from the blood filter after completing the blood treatment session. It further relates to a medical treatment apparatus having a control device with which a method for removing a first fluid from a blood filter is executable, a digital storage medium, and a computer program product.

11 Claims, 3 Drawing Sheets

(56) References Cited

FOREIGN PATENT DOCUMENTS

| | | |
|---|---|---|
| DE | 4240681 | 6/1994 |
| EP | 1539271 | 6/2005 |
| EP | 1892000 | 2/2008 |
| EP | 2535065 | 12/2012 |
| EP | 2745864 | 6/2014 |
| JP | 2004-313522 | 11/2004 |
| JP | 2012-152285 | 8/2012 |
| WO | WO 2004/033001 | 4/2004 |
| WO | WO 2010/121819 | 10/2010 |
| WO | WO 2013/017239 | 2/2013 |

OTHER PUBLICATIONS

English Translation of International Search Report for International Application No. PCT/EP2015/064833, dated Sep. 14, 2015, 6 pages.
EP 1892000, Machine Translation—Espacenet machine translation (Year: 2008).
JP 2004-313522, Machine Translation—Espacenet machine translation (Year: 2004).

METHOD FOR REMOVING FLUID FROM A BLOOD FILTER AFTER COMPLETING A BLOOD TREATMENT SESSION BY MEANS OF FLOW INCREASE AND TREATMENT DEVICE FOR CARRYING OUT SAID METHOD

CROSS REFERENCE TO RELATED APPLICATIONS

This application is a divisional application of and claims priority to U.S. patent application Ser. No. 15/322,840, filed on Mar. 30, 2017, which is the national stage entry of International Patent Application No. PCT/EP2015/064833, filed on Jun. 30, 2015, and claims priority to Application No. DE 10 2014 109 136.1, filed in the Federal Republic of Germany on Jun. 30, 2014, the disclosures of which are express incorporated herein in its entirety by reference thereto.

FIELD OF THE INVENTION

Aspects of the present invention relate to a method and apparatus for removing fluid from a blood filter for the extracorporeal blood treatment of a patient after completing the blood treatment session.

BACKGROUND

Blood filters and extracorporeal blood circuits are usually disposables and are disposed of after their use. Disposing is cost-intensive and is to be paid for by weight of waste. For this reason, and also in order to reduce the risk of contamination, these disposables are thus emptied from fluid and in particular from blood before being disposed of.

SUMMARY

Aspects of the invention relate to methods as well as suitable apparatuses for removing fluid from a blood filter or a blood chamber hereof and optionally from an extracorporeal blood circuit connected herewith.

Thus, a method for removing fluid, in particular blood, from a blood filter used for the blood treatment of a patient after completing the blood treatment session is proposed. The blood filter comprises a blood chamber and a dialysate chamber between which a membrane is arranged, wherein the blood chamber is connected for the blood treatment with an arterial blood line which leads to the blood chamber and a venous blood line which leads away from the blood chamber as well as a dialysis fluid inlet line which leads to the dialysate chamber and a dialysate outlet line which leads away from the dialysate chamber. The method encompasses displacing the fluid from the blood chamber by introducing substitute or a dialysis fluid into the arterial blood line, preferably upstream of the blood chamber.

In some aspects, the control device, which may also be or embodied as a regulating device, is suitable and provided and/or designed and/or configured for executing the method in interaction with a medical blood treatment apparatus. It can optionally comprise further devices such as, for example, storage devices, addition devices, automated signaling devices and so on.

In some aspects, the medical treatment apparatus (hereafter also in short: treatment apparatus) comprises at least one extracorporeal blood circuit with a line interior. It is further equipped with at least one blood pump for conveying blood within the line interior of the extracorporeal blood circuit, the blood pump being arranged at or in the extracorporeal blood circuit. In addition, it comprises at least one device, e.g. a conveying device or a substitute or dialysis fluid pump, provided for introducing substitute or dialysis fluid into the arterial blood line. Moreover, it comprises a control or regulating device.

In some aspects, a storage device, in particular a digital one, in particular a non-volatile one (denoted here also as carrier), in particular a disk, RAM, ROM, CD, hard disk, USB stick, flash card, SD card, or EPROM, in particular with electronically or optically readable control signals may interact with a programmable computer or computer system such that the mechanical steps of the herein described method are prompted.

In doing so, all or some of the steps of the method which are executed by the machine may be prompted.

In some aspects, a computer program product comprises a volatile program code or a program code saved on a machine-readable storage device for prompting the mechanical steps of the method when the computer program product runs on a computer.

The term machine-readable storage device, as used herein, denotes in certain embodiments a carrier which contains data or information which is interpretable by software and/or hardware. The carrier may be a data carrier such as a disk, a CD, DVD, a USB stick, a flashcard, an SD card an EPROM and the like.

In some aspects, a computer program comprises a program code for prompting the steps of the method that are carried out or executed by the machine when the computer program runs on a computer.

Hereby, all, several or some of the mechanically executed steps of the method may be prompted.

In some aspects, a computer program product can be understood as, for example, a computer program which is stored on a data carrier, an embedded system as a comprehensive system with a computer program (e.g. an electronic device with a computer program), a network of computer-implemented computer programs (e.g. a client-server system, a cloud computing system, etc.), or a computer on which a computer product is loaded, executed, saved or developed.

In some aspects, a computer program can be understood as, for example, a physical software product, which is ready for distribution and contains a computer program.

It also applies for the computer program product and the computer program that all or some of the steps of the method that are executed by the machine are prompted.

In the following embodiments, the use of the expression may be or may have and so on, is to be understood synonymously with preferably is or preferably has, respectively, and so on, and is intended to illustrate exemplary embodiments.

Whenever a numerical word is mentioned herein, the skilled in the art understands this as an indication of a numerical lower limit. Provided it does not lead to any contradiction discernible for the skilled person, the skilled person in these cases implicitly understands for example "one" always as "at least one". This understanding is also encompassed by the present invention as well as the interpretation that a numeric word, for example, "one" can alternatively be meant as "exactly one", wherever this is technically possible in the view of the skilled person. Both are encompassed by the present invention and apply to all used numerical words herein.

Advantageous developments of the present invention are each subject of dependent claims and embodiments.

Embodiments may exhibit one or more of the features named hereafter in any technically possible combination.

In some embodiments, the method serves to partially, in others to completely remove blood from a blood filter used for the blood treatment of a patient and/or from the blood circuit after completion of the blood treatment session.

The utilized blood filter is in some embodiments a hemodialyzer.

The membrane arranged between the blood chamber and the dialysate chamber is in certain embodiments a semi-permeable membrane.

In specific embodiments, the venous blood line leads from the blood chamber of the blood filter to a venous blood chamber (herein also denoted as venous air separation chamber) and/or a venous connection point or device or access device.

In certain exemplary embodiments, the arterial blood line leads from an arterial connection point or device or access device to a blood chamber of the blood filter.

In some exemplary embodiments, the method encompasses displacing fluid from the blood chamber by introducing substitute or dialysis fluid into the arterial blood line with a flow of substitute or of the dialysis fluid, which at least in phases, is over the average and/or over the maximum substitute flow of the previous blood treatment.

In some particular exemplary embodiments, the method encompasses displacing the fluid from the blood chamber by introducing a substitute or dialysis fluid into the arterial blood line with a flow rate which, at least in phases, exceeds 150 ml/min, 200 ml/min, 250 ml/min, 300 ml/min, 350 ml/min, 400 ml/min, 450 ml/min, 500 ml/min, 550 ml/min and/or is equal to or less than 600 ml/min.

In some exemplary embodiments, an introduced substituate or dialysis fluid, for the purpose of displacing the fluid from the blood chamber, is led with a first flow into a buffer tank and with a second flow out of the buffer tank. The first flow rate is higher than the second one.

In certain exemplary embodiments, the first flow of the substituate is achieved by the blood pump and/or by sending or delivering suitable signals to the blood pump.

In some exemplary embodiments, the second flow is obtained by a pressure-generating device. This can be a pump, a compressor or the like. The compressor may be an air compressor. The pressure-generating device may be arranged to increase by air the pressure prevailing in the buffer tank, preferably so that the liquid present in the buffer tank is expelled under the second flow out of the buffer tank.

In specific exemplary embodiments, the second flow is achieved by a device (preferably controlled or regulated), which actuates a valve, which in turn either establishes or prevents a fluid communication between the interior of the buffer tank and the exterior of the latter, depending on how the device is being controlled. The pressure compensation established in this manner may effect, together with force acting on the fluid, the desired second flow of the fluid.

In some particular exemplary embodiments, the buffer tank is arranged downstream of the blood chamber.

In certain exemplary embodiments, the buffer tank is a single-needle chamber of a blood cassette.

Such a cassette is exemplarily described in the WO 2010/121819 A1 of the applicant of the present application. Its relevant content is hereby thoroughly incorporated, by reference, as a subject matter also of the present application Such a blood cassette may comprise at least a housing body, preferably made of a rigid resin, having at least one, two or more chamber(s) integrated into the housing body for receiving medical fluids, at least one channel integrated into the housing body for receiving and/or conducting a medical fluid and at least one valve device completely or partially integrated in the housing body for controlling or regulating a fluid flowing through the blood cassette.

Such a blood cassette may comprise at least one single-needle chamber for receiving blood downstream of the blood filter Such a single-needle chamber may encompass or have at least one single-needle valve, or be in fluid connection thereto, which controls or regulates the inflow or outflow of blood in the single-needle chamber. Examples of a single-needle chamber and a single-needle valve are exemplarily described in WO 2010/121819 A1, whose content is incorporated, by reference, as a subject matter of the present invention as well.

The single-needle chamber may—just as any other buffer tank—be connected to a compressed air source. Thereto, the latter may comprise preferably a sterile membrane through which or through the layer of which air or sterile air may be introduced into the single-needle chamber by the compressed air source. The increase of pressure (in an upper area of the single needle chamber) effected or caused by the introduction of sterile air into the single-needle chamber leads to discharging the fluid (which is present in the bottom area of the single-needle chamber) out of the single-needle chamber. The fluid may be discharged with the second flow by a corresponding control or regulation of the compressed air source and/or by actuating the respective valve. The second flow may hereby be set to the desired reinfusion flow. The latter may hereby be decoupled from the first flow which leads into the single-needle chamber.

Such a blood cassette may comprise at least one of its surfaces a covering device or cover which is preferably part of at least one integrated valve device.

By such blood cassettes, the cover device may be at least in one section connected with the housing body in a force-fit and/or form-fit and/or bonded manner.

By such blood cassettes, the cover device may be connected with the housing body by at least one closed weld.

In some exemplary embodiments, the control and/or regulating device is configured to effect, in interaction with a medical blood treatment apparatus, a blood treatment and a subsequent displacement of fluid, in particular blood, from the blood chamber by an introduced substitute or an introduced dialysis fluid with a predetermined, preferably fluctuating or non-constant flow thereof, preferably through the blood filter, e.g. by delivering a corresponding signal to the blood pump. The herein denoted predetermined flow, may generate a flow of introduced substituate or introduced dialysis fluid, e.g. in the patient, which assumes in average 150 ml/min, when appropriate+/−30%, 20% or 10% thereof. Said average may apply over or through the entire duration of the blood treatment including over or through the subsequent displacement of the fluid.

In some particular exemplary embodiments, the medical treatment apparatus comprises or is, preferably, in fluid communication connected thereto, a buffer tank for receiving fluid (pure or mixed) which is displaced from the blood chamber. The control device may be configured to use the buffer tank in interaction with pumps, clamps or other such devices.

In some particular exemplary embodiments, the buffer tank is arranged downstream of the blood chamber.

In specific exemplary embodiments, the medical treatment apparatus and/or the blood filter are/is connected with a blood cassette, wherein the buffer tank is a single needle chamber of the blood cassette.

In certain exemplary embodiments of the method, at least one patient clamp is closed to stop a flow of blood within the arterial blood line and/or the venous blood line. In some particular embodiments, a single-needle valve is additionally closed.

In some exemplary embodiments of the method, an arterial blood line is connected with a venous blood line for the purpose of emptying the blood filter. In specific embodiments, a connection between the arterial blood line and the venous blood line remains completely undone or is not established.

In some particular exemplary embodiments, the connection between the arterial blood line and the venous blood line is established, in particular exclusively for the purpose of emptying the blood filter.

In some particular embodiments of the method, the method encompasses detecting a qualitative change of the content of the line interior of the extracorporeal blood circuit.

In some embodiments of the method, a predetermined amount of substitute or dialysis fluid is introduced into the line interior of the extracorporeal blood circuit by operating a conveying device, for example, the blood pump, the substitute pump or the dialysis fluid pump.

In some particular embodiments of the method, a substitute (alternatively denoted as substitute fluid) or dialysis fluid is conveyed until the detection device detects a substitute or a dialysis fluid, in a predetermined measurement, in the line interior of the extracorporeal blood circuit.

In some embodiments of the method, the detection device is arranged with a predetermined distance to a venous access device. In these embodiments the method further encompasses conveying the content of the line interior of the extracorporeal blood circuit across or along the predetermined distance to the venous access device after dialysate has been detected at or by the detection device.

In some particular embodiment, blood contained in the line interior of the extracorporeal blood circuit is inserted into the vascular system of the patient via the venous access device.

In some particular embodiments, the method further encompasses inserting, entering or introducing air and substitute into the extracorporeal blood circuit, for example after completion of a blood treatment session.

A blood treatment session may be, for example, a treatment unit by hemodialysis, hemofiltration, hemodiafiltration and/or a cell separation method and it is directed to the treatment and/or purification of blood. For performing such a blood treatment, a suitable blood treatment apparatus is used.

A blood treatment apparatus which is suitable for executing the method comprises in some embodiments an extracorporeal blood circuit with a line interior or is connected therewith, at least one conveying device for introducing and/or conveying at least two fluids in the line interior of the extracorporeal blood circuit, and for example a device for treating the blood of the patient, such as one or several blood filters and/or one or several dialyzers and/or one or several adsorbents. It may further comprise containers for storing fluids, elements for introducing the fluids, such as for example tube elements and/or valves, as well as further devices such as for example an air separation chamber or bubble trap for removing air from the blood during the blood treatment and/or sensors and/or detectors for detecting various relevant parameters, such as, for example, a pressure in the extracorporeal blood circuit.

Conveying devices, as mentioned herein, include membrane pumps, tube pumps, roller pumps and so on. The blood pump, a substituate pump and/or dialysis fluid pump may be embodied, e.g., as a tube pump or a roller pump. However, also a different type of pump may be used, e.g. a membrane pump, particularly a high-precision metering membrane pump.

A conveying device for dialysis fluid or substituate may be a second conveying device, i.e. a conveying device which is different from the blood pump. The blood pump may, however, also be designed such that it fulfils both the function which is typical for a blood pump and the function of introducing substituate into the line interior and/or conveying line content. Whenever a conveying device for introducing substituate or dialysis fluid is mentioned hereafter, just for the purpose of better legibility, this relates to the blood pump or a different conveying device therefrom. Both versions are equally encompassed by the present invention.

In certain exemplary embodiments, the substituate is increased, after completion of the treatment and/or for flushing the blood filter of blood, to a level which is above that or any value which has been assumed during the blood treatment. In order to limit the average reinfusion velocity, low-flow phases follow, in these embodiments, high-flow phases such that the desired average reinfusion flow rate of 150 ml/min for example is established.

The method encompasses in certain embodiments the step of introducing or entering air into the line interior of the extracorporeal blood circuit for the purpose of emptying it from fluid, by operating the blood pump. The air may for example be atmospheric air. The present invention is, however, not intended to be limited to the sole use of air, but include all gaseous fluids instead of air which are suitable for the purposes of the present invention.

Entering air into the line interior of the extracorporeal blood circuit after termination of the blood treatment session may take place exclusively or in a supporting way by the blood pump, by the second conveying device or by a source of compressed air.

Combinations of the before-mentioned options are also encompassed, also passively allowing air to enter.

Introducing substituate or dialysis fluid into the line interior of the extracorporeal blood circuit takes place, as described above, in some particular embodiments by operating the blood pump and/or the conveying device.

The blood pump may convey substituate by drawing it from a supply line from a container for the substituate, wherein the supply line enters into the extracorporeal blood circuit upstream of the suction side of the blood pump. For this, for example a mouth with a tube clamp which is provided in the arterial branch of the extracorporeal blood circuit may be provided.

If it is intended that the blood pump introduces and conveys both blood and substituate into the extracorporeal blood circuit, the method may be executed with just one pump. Hereafter embodiments are described in which a blood pump and a second conveying device are used. The following description shall simplify the understanding of the principles and functions of the individual components.

A substituate may be for example any commonly known substituate or dialysis fluid which is used during a blood treatment such as, e.g., a hemodiafiltration, preferably a solution or isotonic saline solution which has already been used during the blood treatment session which thus was already introduced or introducible into the extracorporeal blood circuit via a fluid connection, such as for example a 0.9% NaCl solution.

In a further preferred embodiment, detecting a qualitative change of the content of the line interior of the extracorporeal blood circuit by at least one detection device which is arranged in or at a section of the extracorporeal blood circuit is encompassed.

The qualitative change may relate to one or several areas or sections of the extracorporeal blood circuit, for example an area or section in which the detection device is arranged.

A qualitative change of the content of the line interior includes a change or amendment in the composition of the content of the line interior, such as for example a change of the individual parts of blood, substitute and/or air in the line interior or a section hereof, in relation to each other. Also the lack of a fluid which was previously present may represent a change in the composition. A qualitative change may also be a transition from blood to substitute. Such changes may for example be easily detected because of an optical change of the content, such as a brightening or darkening of the content.

The detection device which is arranged in a section of the extracorporeal blood circuit may for example be an optical sensor which detects an optical change of the content of the line interior or a property of its content. Further suitable sensors include pressure, conductivity sensors and sensors for detecting a change in the density of the content of the line interior of the extracorporeal blood circuit, without being limited hereto.

The section of the extracorporeal blood circuit may be an arterial and/or venous section of the extracorporeal blood circuit. The arterial section relates to a section of the extracorporeal blood circuit through which blood flows from the vascular system of the patient in the direction towards the blood treatment device or towards the blood filter. The venous section relates to the section of the extracorporeal blood circuit through which blood flows from the blood treatment device or from the blood filter back to the vascular system of the patient.

In an also preferred development or refinement of the method, the extracorporeal blood circuit encompasses at least one access device which is connectable with a section of the vascular system of the patient, and the method encompasses disconnecting the extracorporeal blood circuit from the vascular system of the patient, in particular in the area of a first, for example arterial, access device, in particular at an end of the extracorporeal blood circuit.

Disconnecting the extracorporeal blood circuit from the vascular system of the patient means interrupting a connection between the extracorporeal blood circuit and the vascular system of the patient in a section of the extracorporeal blood circuit, for example at an end hereof. In doing so, the interruption may take place both at the arterial and at the venous section, disconnecting the arterial section of the extracorporeal blood circuit is preferred.

Disconnecting in the area of the first access device may be understood as for example pulling out the arterial connection needle of a double-needle access.

Disconnecting may also be understood as interrupting the flow connection between the arterial section of the extracorporeal blood circuit and the arterial connection needle.

In the case of the single-needle version, disconnecting may be understood as interrupting the connection between the arterial leg of the Y-shaped section of the extracorporeal blood circuit and the only connection needle which is connected with the vascular system of the patient. The open lumen of the arterial leg of the Y-part may be closed in any manner (manually, mechanically, automatically and so on) after being separated.

Alternatively or in addition, the same may be applied to the venous section of the extracorporeal blood circuit and the venous access to the vascular system of the patient.

An addition point for the extracorporeal blood circuit for substitute into the line interior of the extracorporeal blood circuit may be arranged in the arterial and/or the venous section of the extracorporeal blood circuit. It is preferred to arrange the addition point in a section of the extracorporeal blood circuit which is flown through upstream of the blood treatment device, as well as for example of the blood filter.

Suitable examples for an addition point include an opening/closing valve, a stop cock, a connectable branch line of a branched section of the extracorporeal blood circuit and so on.

A predetermined substitute amount or dialysis fluid amount can correspond to a certain feed volume and/or a certain path length of the line interior of the extracorporeal blood circuit along which the content is conveyed and can, for example, take place by operating a highly precisely metering membrane pump.

The substitute amount or the dialysis fluid amount can preferably be predetermined as a magnitude, for example as a volume with a preset value and unit. The absolute magnitude of the substitute amount can preferably be stored and/or be insertable for example in a control device of the treatment apparatus. The substitute amount can preferably be exactly conveyed within the frame of the technical precision.

In order to predetermine an exact amount of substitute, e.g., technical specifications of the utilized extracorporeal blood circuit, such as for example the inner volumes of the tube set, can be stored or entered in (to) the control device. By the technical specifications of the individual components of the extracorporeal blood circuit, for example a required feed time and/or a feed volume can be calculated.

A limited amount of substitute or dialysis fluid may be for example an amount of substitute liquid which was chosen by the operating personnel's empirical values. Preferably, a limited amount of fluid can be introduced and conveyed for so long until substitute is detected in the line interior of the extracorporeal blood circuit at a further detection device. A limited substitute amount thus does not have to be exactly known and/or correspond to a certain feed volume. A limited amount of substitute may, however, be indirectly limited by the inner volume of the components of the extracorporeal blood circuit through which the substituate amount flows, in particular the inner volume of the section between the addition point for substituate and/or the blood treatment device and a further detection device. The volume is hereby thus determined in the sense of limited, however, without being exactly known, and without being expressible for example in milliliters and/or without having been stored or being enterable in a controller. Introducing a limited amount of substitute may be of advantage, e.g., if the type of the filter of a blood treatment device or its capacity is unknown or incorrectly stated.

In doing so, the substitute of a storage container provided for this may be introduced into the extracorporeal blood circuit at the addition point for the substitute via corresponding line systems of the extracorporeal blood circuit.

The detection device is defined as above and may be arranged for example in the venous section of the extracorporeal blood circuit, e.g., between the blood treatment device and the venous access device to the vascular system of the patient and in particular between a drip chamber in the venous section and the venous access device.

The detection device may detect the occurrence of substituate in a certain section of the line interior of the extracorporeal blood circuit, for example by an optical change of the content of the line interior.

If or when the detection device detects the occurrence of air or substituate in the line interior of the extracorporeal blood circuit, conveying the air-substituate-blood content may be stopped.

This may take place by stopping the respective conveying device.

Further, in another embodiment of the method it is preferred to arrange the detection device with a predefined distance to a second access device and to convey the content of the line interior along the predefined distance to the access device after substituate or a predetermined transmission was recognized at the detection device.

In a further preferred embodiment of the method, the blood contained in the line interior of the extracorporeal blood circuit is returned into the vascular system of the patient—in particular substantially completely—via the second access device. The term substantially completely returned means herein that the blood present in the line interior of the extracorporeal blood circuit is removed nearly without residues from the extracorporeal blood circuit. The blood residues possibly remaining in the extracorporeal blood circuit for technical reasons such as wetting behavior or the blood residues remaining in the drip chamber are hereby to be regarded as negligibly small.

Returning blood into the vascular system of the patient may take place if or when an end of the extracorporeal blood circuit, such as for example the end of the venous section, e.g., the venous connection needle, is connected with the vascular system of the patient. This connection may be maintained or re-established after the end of the blood treatment session.

Due to the fact that the method as described above is executable with the treatment apparatus, it is referred to the respective embodiments as described above in order to avoid repetition.

A development of the treatment apparatus provides the arrangement of at least one detection device for detecting at least one change of the content of the line interior of the extracorporeal blood circuit or one property of the content in a section of the extracorporeal blood circuit. A property of the content may be a composition, a physical, chemical or biological magnitude, for example a transparency, a pH value and much more suchlike. A suchlike detection device may correspond to the one described above, thus it is referred to its above description in order to avoid repetition.

A treatment apparatus may, without being limited hereto, be suitable and/or configured to perform hemodialysis, hemofiltration, hemodiafiltration and separation methods.

One or more of the herein mentioned advantages may be achieved via some embodiments.

Thus, the present invention may contribute in certain embodiments to an improvement of the effectivity of AV blood return.

An advantage which can be achieved in some particular embodiments is that a contamination risk during further handling or disposing of the blood filter and/or of the extracorporeal blood circuit may be avoided or diminished, because after completion of the method, there isn't any blood remaining in the blood filter anymore or its amount has been markedly reduced.

Furthermore, the gross waste weight of the blood filter and/or of the extracorporeal blood circuit may be reduced. As a disposal of contaminated disposables such as blood filter and extracorporeal blood circuit is calculated according to weight, costs may thus advantageously be saved.

Emptying at least the blood filter, particularly from blood, may in certain embodiments take place without substantial interaction or without any interaction by the user, e.g., the doctor, at least until the blood filter is removed from the treatment apparatus. A side effect is that the error rate is low. In addition, the user has time for other activities during emptying. This contributes to easing the workload and saving time altogether.

Some embodiments may further advantageously be used for safe removal of blood from the extracorporeal blood circuit for a treatment apparatus for the extracorporeal blood treatment of a patient after completing a blood treatment session: Since substituate is present in the line interior of the extracorporeal blood circuit after completing the blood treatment session, the blood present in the line interior of the extracorporeal blood circuit can be removed from the extracorporeal blood circuit. This may take place without the risk of introducing air into the body of the patient.

Introducing substituate with increased pressure or flow, as described supra, may further contribute to cleaning a blood filter with different inner capillary diameters from blood, which would be technically hardly realizable by only running air through it, due to the lesser pressure drop across the already air-filled capillaries as opposed to the capillaries which are still filled with blood.

Besides, it may also be possible to minimize foaming, for example at the outlet of the blood filter, by using substituate there, i.e. in particular a liquid, and not only a gas (e.g., air) for displacing blood or emptying.

Due to the fact that the usual, average reinfusion flow of e.g. 150 ml/min should not be exceeded during the flushing, the well-being of the patient and the integrity of the vascular system and particularly a shunt of the patient shall not be impaired due to said flushing. Significantly higher flushing flows than the afore-mentioned 150 ml/min may indeed occur. However, this flushing flow does not correspond in certain embodiments to the reinfusion velocity or to the reinfusion flow with which blood is being reinfused into the patient, due to the fact that the buffer effect of the buffer tank and to the fact that the outflow therefrom is less than the inflow into the buffer tank.

The inventors have recognized that the effectiveness of the flushing or rinsing of blood from the blood filter increases with an increasing flow. This is achieved in certain embodiments.

Since the method may be executed directly after a blood treatment session has come to an end, it is simply and easily executable and does not require any technically complex, time- and/or cost-intensive steps.

The method may advantageously be executed with the substituate or dialysis fluid which is used or present anyway in a blood treatment, such as for example an isotonic saline solution, e.g., a 0.9% NaCl solution. This in turn advantageously contributes to saving costs and time.

Further, the method may enable a removal of blood from the arterial section of the extracorporeal blood circuit and in particular from the arterial connection needle and the return of the blood into the vascular system of the patient. The step of retrogradely pushing out the blood present in the arterial connection needle with the aid of, e.g., a syringe which is filled with saline solution may thus advantageously be avoided.

The method may thus offer the advantage of basically completely regaining the blood present in the line interior of an extracorporeal blood circuit after that has been used for a blood treatment for the patient.

The approach may ensure that no air enters the vascular system of the patient during emptying. Furthermore, no foaming in the area of a blood filter present in the extracorporeal blood circuit can occur with this method, which would hamper emptying the blood from the extracorporeal blood circuit. Still, blood remaining in the blood filter or in the extracorporeal blood circuit constitutes a contamination risk.

Another advantage which is achievable in some embodiments is that for the first time a simple and safe method is proposed for notably reducing the remaining weight of both the blood filter and the blood circuit after termination of the blood treatment. It is thus specified how both the blood chamber of the blood filter and the blood circuit are emptied, wherein this may take place in some embodiments completely or nearly completely automatically; in any case this may take place with little activity of the medical personnel. This is achieved not least due to the optimized chronology of emptying the blood chamber on the one hand and, on the other hand, the remaining sections of the blood filter and the blood circuit which are also emptied in some embodiments.

BRIEF DESCRIPTION OF THE DRAWINGS

Hereafter, the method is exemplarily described by preferred embodiments with reference to the accompanying drawing. In the drawing, the following applies.

DETAILED DESCRIPTION

Figure 1:
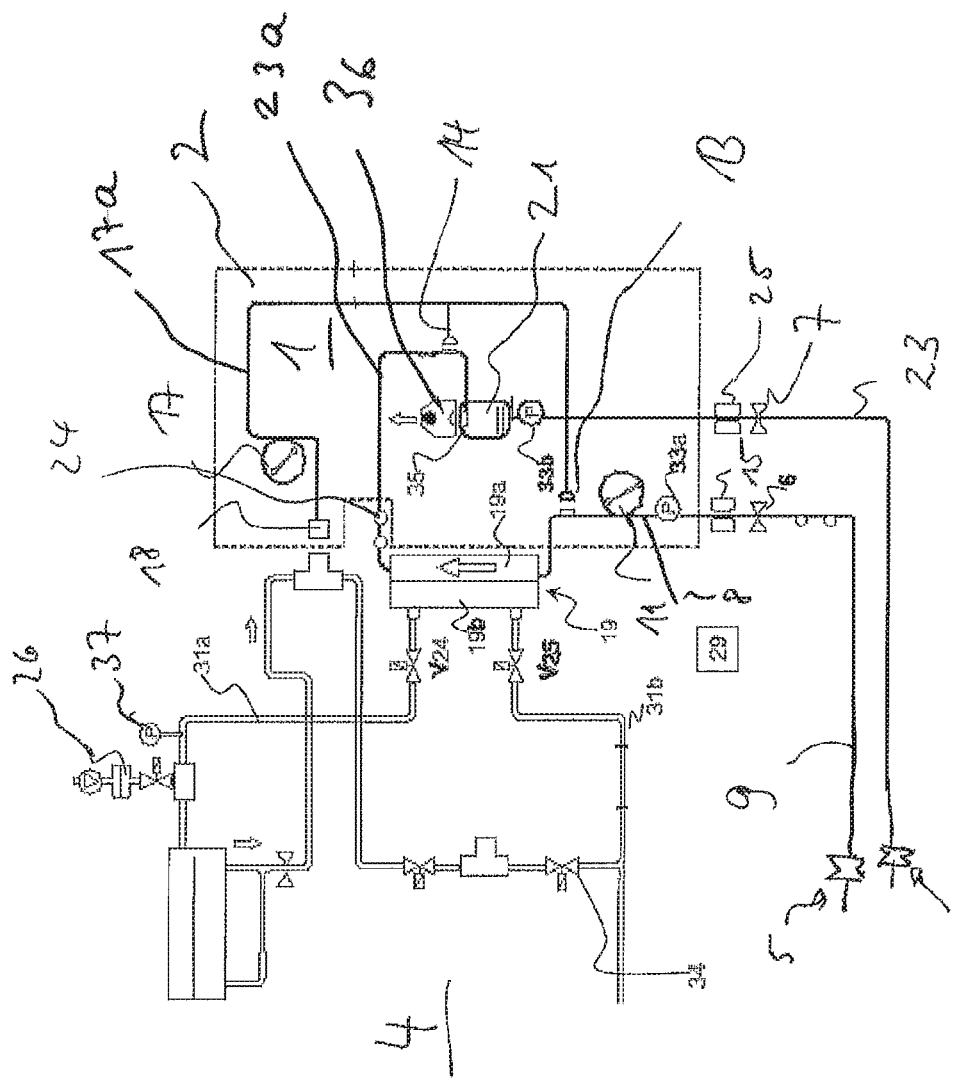
FIG. 1 illustrates in a schematically simplified manner sections of a medical treatment apparatus having a blood cassette for performing the method in a first embodiment.

FIG. 1 shows an extracorporeal blood circuit 1 which is connected, by double-needle access, to the vascular system of the patient (not shown). The blood circuit 1 is disposed in section thereof in or on the blood cassette 2 (exemplarily as described above). The blood circuit 1 is connected to a treatment apparatus 4.

The blood circuit 1 comprises an arterial patient hose clamp 6 and an arterial connection needle 5 (as an example of an access device) of an arterial section or of an arterial patient or line blood line 9. The blood circuit 1 further comprises a venous patient hose clamp 7 and a connection needle 27 (as an example of a further or second access device) of a venous section or of a venous patient line or blood line 23.

A blood pump 11 is provided in the arterial section 9, a substitute pump 17a is connected to a substitute line 17. The substitute line 17a can be connected with a substitute source through a, preferably automatic, substitute port 18. By the substitute pump 17, substitute may be introduced via pre-dilution or via post-dilution through associated lines 13 or 14 into line sections, e.g., into the arterial section 9 or into a venous section 23a (between a blood chamber 19a and a single needle chamber 36 (see below) of the blood circuit 1.

A blood filter 19 is provided in or with the blood circuit 1. It comprises a blood chamber 19a which is connected with the arterial section 9 and with the venous section 23. A dialysate chamber 19b is connected with a dialysis fluid inlet line 31a which leads to the dialysate chamber 19b and with a dialysate outlet line 31b which leads away from the dialysate chamber 19b.

The dialysis fluid inlet line 31a optionally comprises a valve V24 by which the flow within the dialysis fluid inlet line 31a may be stopped. The dialysate outlet line 31b optionally comprises a valve V25 by which the flow within the dialysate outlet line 31b may be stopped.

The dialysis inlet line 31a is further optionally connected to a compressed air source 26 by another internal valve of the apparatus. The compressed air source 26 may be provided as a part or component of the treatment apparatus 4 or as a separate part thereof. A pressure sensor 37 may be provided downstream of the compressed air source 26.

For performing the method aiming to empty the blood chamber 19a of the blood filter 19 after completion of the treatment, the arterial patient hose clamp 6 may be closed, the venous patient hose clamp 7 may be opened and/or the blood pump 11 (exemplarily designed as a roller pump) may be stopped and a substituate or dialysis fluid may be introduced by a substituate pump 17 through the addition point 13 in pre-dilution of the blood circuit 1 and of the blood chamber 19a.

Alternatively or in addition, it is possible not to introduce the substituate by operating the substituate pump 17 but by operating the blood pump 11. Thereto, the arterial patient hose clamp 6 is closed and substituate is introduced into the extracorporeal blood circuit 1 via a supply line 8 from a storage container for the substituate.

The achieved substituate-blood content is conveyed along the line interior of the extracorporeal blood circuit 1 by operating the blood pump 11 and/or the substituate pump 17. It is as well pressed or conveyed through the blood filter 19, the venous air separation chamber 21 and a venous section 23 of the extracorporeal blood circuit 1 in order to remove the blood from the extracorporeal blood circuit 1 in the direction towards the venous connection needle 27 from the blood filter 19.

A venous substituate-blood detector 25 is optionally arranged in the venous section 23 of the extracorporeal blood circuit 1 as a further example of a detection device which detects the occurrence of substituate at a predetermined position of the line interior of the extracorporeal blood circuit 1. The blood pump 11 and/or the substituate pump 17 continue conveying the substituate-blood content until the blood in the venous section 23 of the extracorporeal blood circuit 1 is removed from it and returned to the vascular system of the patient via the venous connection needle 27, and/or until substituate is detected in the line interior at the venous substituate-blood detector 25. The conveying effort of all pumps is stopped at this point. An optical and/or acoustical signal can be output.

Controlling or regulating the treatment apparatus 4 may be carried out by a control or regulating device 29.

The arrangement of FIG. 1 encompasses an optional detector 15 for detecting air and/or blood. The arrangement of FIG. 1 encompasses further one or two pressure sensors 33a, 33b at the illustrated points in FIG. 1.

The introduced substituate may be temporarily stored in a buffer tank or container, from which it will or can be discharged at a lower flow rate than that with which it has been introduced into the buffer tank.

The single needle chamber 36 is particularly taken into consideration as buffer tank in the arrangement of FIG. 1. The single needle chamber 36 may be an active or non-active part in the blood circuit by correspondingly switching an optional single needle valve 35, which separates the single needle chamber 36 preferably from further, in particular from all further blood conducting structures. When the single needle chamber 36 is accessible—by opening the single needle valve 35—for blood or another fluid which flows out of the venous section 23a downstream of the blood filter 19 and when at the same time a flow-through of blood or of fluid along the single needle chamber 36 is prevented exemplarily by closing the patient hose clamp 7, then the blood may first be buffered or stored in the single needle chamber 36 before it leaves, with a desired flow rate, the single needle chamber 36 towards the venous patient hose clamp 7, after the venous patient hose clamp 7 has been opened.

Figure 2:
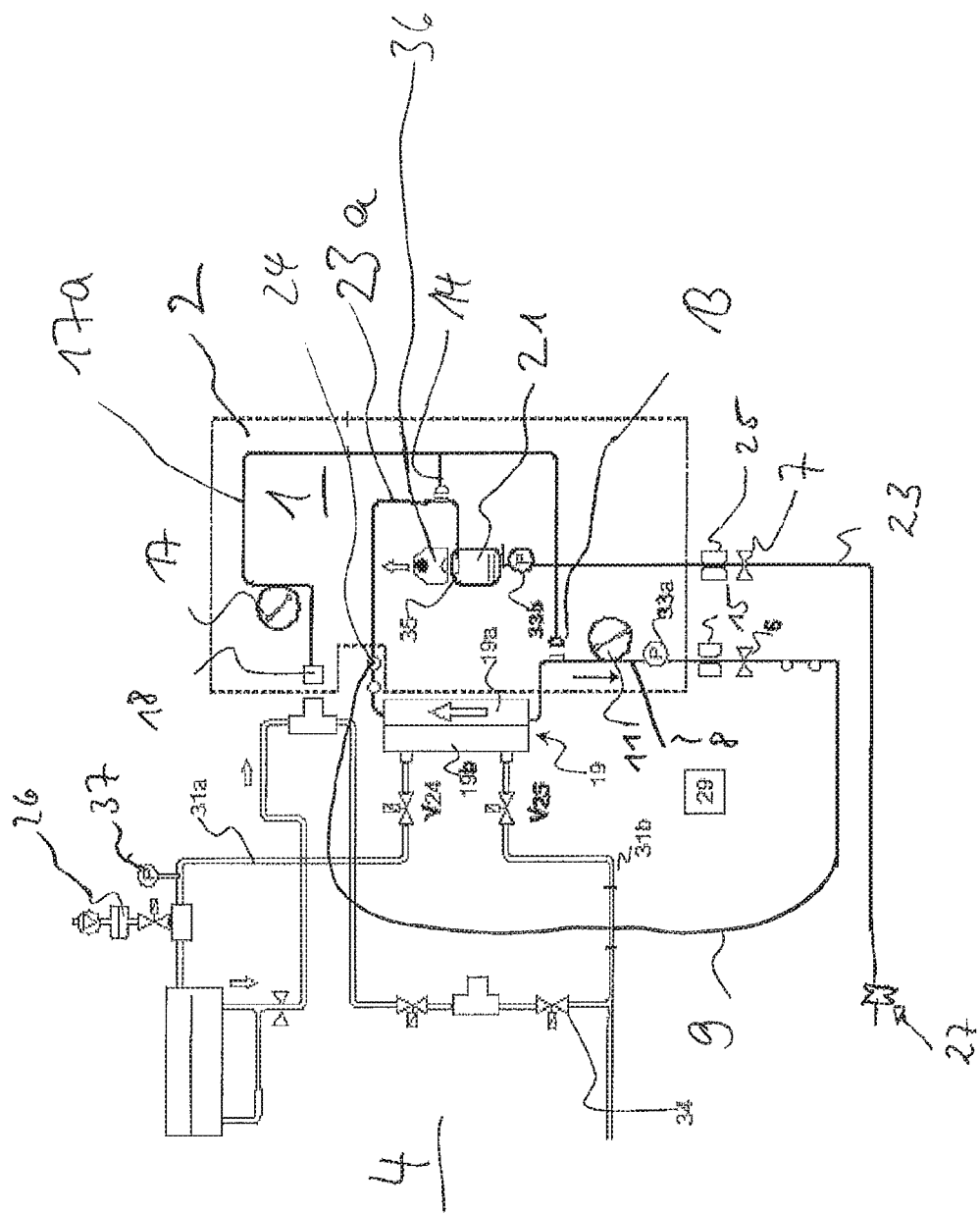
FIG. 2 illustrates the medical treatment apparatus of FIG. 1 when or while performing the method in a second exemplary embodiment.

Alternatively, it may exemplarily be proceeded as illustrated in FIG. 2:

The extracorporeal blood circuit 1 is disconnected from the vascular system of the patient by, e.g., removing the arterial connection needle 5 from the arm of the patient. In any case however, the arterial blood line 9 is connected upstream of the blood filter 19 at a connection point 24 with the venous section 23a. The arterial patient hose clamp 6 remains open. Due to the pressure of the substitute pump 17, substitute is conveyed along the directions of the two arrows both through the blood chamber 19a and through the arterial blood line 9. The blood present in the blood chamber 19a and in the arterial blood line 9 is thus removed in this way from both blood chamber 19a and from the arterial line 9.

In FIGS. 1 and 2, the single needle chamber 36 is used as a buffer tank, in particular during or after a double-needle method by which a patient is connected with the extracorporeal blood circuit 1 by two blood lines 9 and 27. However, it is apparent for the skilled in the art that some embodiments may also be carried out or performed without using a buffer tank. In addition, any other buffer tank may be taken into consideration.

Figure 3:
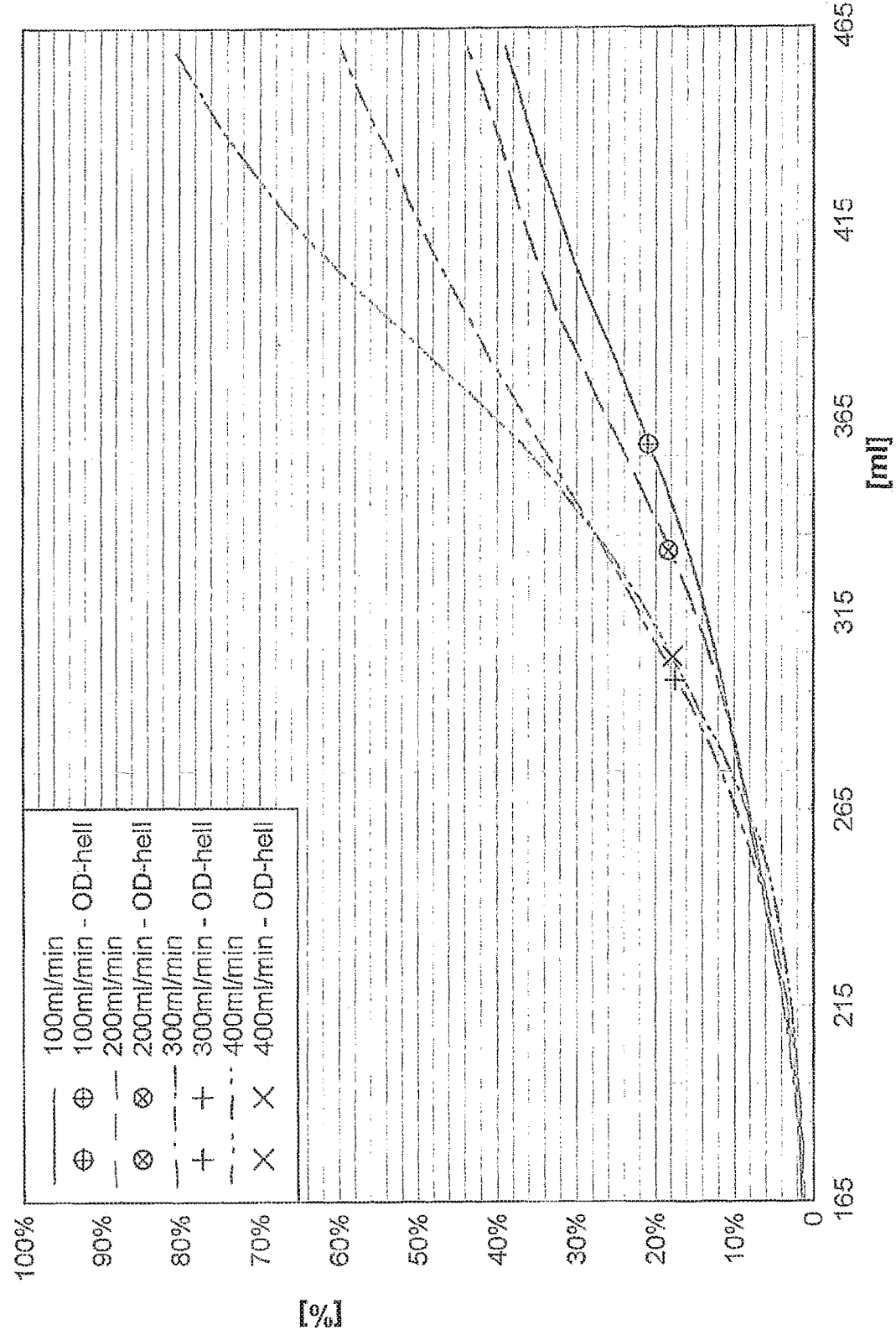
FIG. 3 illustrates the measured transmission (in percent (%)), shown over the reinfusion volume (in milliliter (ml))

FIG. 3 shows the measured transmission (in %) shown over the reinfusion volume (in ml) which was measured by the inventors in an experimental set up using the $FX_{hdf}1000$ dialyzer from or made by the applicant at different substituate flow rates, as indicated in the graph of FIG. 3.

Substitute is sucked in or drawn in arterially in the experimental set up. At the venous blood line 23, see FIG. 1 or 2, a photometer, provided for detecting a transmitted light power, is mounted about 10 cm below or downstream of the venous optical detector 25 and of the venous patient hose clamp 7. The sensor of the photometer has been normalized or standardized on clear, bloodless substitute. The transmission has been detected depending on the rinsing or flushing volume at different substitute flow rates. The hematocrit of the used bovine blood is 30% prior to each experiment.

FIG. 3 shows the advantageous efficiency performed by the method by which higher substitute flow rates than usual are used or practiced for rinsing or flushing.

It is evident that with increasing substituate flow used as rinsing flow, the line content gets clear sooner or the measured transmission increases.

The amount of the blood remaining in the extracorporeal blood circuit decreases when having a predetermined or fixed reinfusion volume.

The respectively selected points in the graphs denote the reinfusion volume by which or at which the detection device, e.g. the optical sensor, does not detect any blood anymore.

The present invention is not limited to the embodiments as described above, they are considered only for illustrative purposes. Furthermore, the invention is not limited to emptying the content or parts hereof while a connection with the vascular system still exists.

REFERENCE NUMERAL LIST 1 extracorporeal blood circuit
2 blood cassette
4 treatment apparatus
5 access device, e.g. arterial connection needle
6 arterial patient tube clamp
7 venous patient tube clamp
8 supply line
9 arterial section or arterial blood line or arterial patient line
11 blood pump
13 addition site for substitute (pre-dilution)
14 addition site for substitute (post-dilution)
15 arterial air/blood detector
17 second conveying device, e.g. a substituate pump
17a substitute line
18 automatic substituate port
29 blood filter
19a blood chamber
19b used dialysate chamber
21 air separator chamber
23 venous section or venous blood line
23a venous section
24 connection site
25 venous substitute blood detector
26 compressed air source
27 access device, e.g. venous connection needle
29 control or regulating unit
31a dialysis inlet line
31b dialysate fluid outlet line
33a, b pressure sensors
35 single-needle valve
36 single needle chamber
37 pressure sensor
V24 valve
V25 valve

What is claimed:
1. A medical treatment apparatus comprising:
at least one extracorporeal blood circuit with a line interior and comprising a blood chamber and an arterial blood line; and
a medical blood treatment apparatus comprising:
at least one blood pump which is arranged along the extracorporeal blood circuit for conveying blood within the line interior of the extracorporeal blood circuit;
at least one device for introducing a second fluid into the arterial blood line; and
a control device configured to, after completing a blood treatment session of a patient using the medical treatment apparatus, control the medical blood treatment apparatus to cause blood to be displaced from the blood chamber by introducing the second fluid into the arterial blood line in phases of high-flow followed by phases of low-flow such that the displaced blood is reinfused to the patient at a desired average reinfusion flow rate.

2. The medical treatment apparatus according to claim 1, wherein the control device is further configured to control the medical blood treatment apparatus to cause a subsequent displacing of a first fluid from the blood chamber by an introduced substituate with a predetermined substituate flow rate through a blood filter between 135 ml/min and 165 ml/min.

3. The medical treatment apparatus according to claim 2, wherein the subsequent displacing of the first fluid from the blood chamber by an introduced substituate with the predetermined substituate flow rate through the blood filter is between 135 ml/min and 165 ml/min in average.

4. The medical treatment apparatus according to claim 1, wherein the control device is further configured to control the medical blood treatment apparatus to perform the blood treatment session of the patient using the medical treatment apparatus.

5. The medical treatment apparatus according to claim 1, wherein the medical blood treatment apparatus further comprises a buffer tank for receiving fluid which has been displaced from the blood chamber, wherein the buffer tank is in fluid communication with the blood chamber.

6. The medical treatment apparatus according to claim 5, wherein the buffer tank is arranged downstream of the blood chamber.

7. The medical treatment apparatus according to claim 5, further comprising a blood cassette, and wherein the buffer tank is a single needle chamber of the blood cassette.

8. The medical treatment apparatus according to claim 1, wherein the second fluid is a substituate fluid or a dialysis fluid.

9. The medical treatment apparatus according to claim 1, wherein the at least one extracorporeal blood circuit further comprises a blood filter comprising the blood chamber and a dialysate chamber between which a membrane is arranged.

10. The medical treatment apparatus according to claim 9, wherein the blood chamber is in fluid communication with the arterial blood line and with a venous blood line.

11. The medical treatment apparatus according to claim 9, wherein the dialysate chamber is in fluid communication with a dialysis inlet line and with a dialysate outlet line.

* * * * *